United States Patent [19]

McDonald

[11] Patent Number: 5,711,317
[45] Date of Patent: Jan. 27, 1998

[54] MULTIPLE FOLDING OF OPTICAL LENS UNIT AND PLACEMENT IN THE EYE

[75] Inventor: Henry H. McDonald, 525 Cordova Street, Pasadena, Calif. 91101

[73] Assignees: Henry H. McDonald; William W. Haefliger, both of Pasadena, Calif.; a part interest

[21] Appl. No.: 680,683

[22] Filed: Jul. 17, 1996

[51] Int. Cl.[6] .................................................. A61B 19/00
[52] U.S. Cl. ........................... 128/898; 606/107; 623/6
[58] Field of Search ........................ 128/898; 606/107; 623/6; 294/1.2

[56] References Cited

U.S. PATENT DOCUMENTS

| 4,573,998 | 3/1986 | Mazzocco | 623/6 |
|---|---|---|---|
| 4,813,957 | 3/1989 | McDonald | 623/6 |
| 4,959,070 | 9/1990 | McDonald | 623/6 |
| 5,100,410 | 3/1992 | Dulebohn | 606/107 |
| 5,171,319 | 12/1992 | Keates et al. | 623/6 |
| 5,190,553 | 3/1993 | Kanert et al. | 606/107 |
| 5,217,464 | 6/1993 | McDonald | 606/107 |
| 5,242,450 | 9/1993 | McDonald | 606/107 |
| 5,275,604 | 1/1994 | Rheinish et al. | 606/107 |
| 5,304,182 | 4/1994 | Rheinish et al. | 606/107 |
| 5,456,687 | 10/1995 | DeVenuto | 606/107 |
| 5,549,614 | 8/1996 | Tunis | 606/107 |
| 5,556,400 | 9/1996 | Tunis | 606/107 |
| 5,578,042 | 11/1996 | Cumming | 606/107 |

*Primary Examiner*—Vincent Millin
*Assistant Examiner*—Kelly O' Hara
*Attorney, Agent, or Firm*—William W. Haefliger

[57] ABSTRACT

The method of inserting a foldable plastic lens unit into the eye that includes folding the lens unit to form at least three folds; grasping the folded unit to hold it in folded state, and then inserting the folded unit into the eye through an opening formed in the eye.

16 Claims, 8 Drawing Sheets

MULTIPLE FOLDING OF OPTICAL LENS UNIT AND PLACEMENT IN THE EYE

BACKGROUND OF THE INVENTION

This invention relates generally to insertion of an artificial lens unit into the eye; and more particularly to creation of a multi-folded lens unit, and grasping of same, for insertion into a very small wound opening in the eye, whereby very rapid lens replacement surgery can be achieved, with minimum disruption of the eye.

There is constant need for improvements in eye surgery, particularly in lens implant surgery, to achieve faster and more efficient lens insertion and positioning, as well as reduced size eye wound openings in the interests of faster healing. There is particular need in these regards, for implants in intraocular lens implant surgery.

Prior techniques are believed not to incorporate or suggest the unusual improvements in method and apparatus which are the subject of the present invention.

SUMMARY OF THE INVENTION

It is a major object of the invention to provide method and apparatus meeting the above needs, and providing for faster, more efficient, and less disruptive lens implant surgery.

Basically, the present method of inserting a foldable plastic lens unit into the eye includes the steps:

a) folding the lens unit to form at least three folds, b) grasping the folded unit to hold it in folded state, and then inserting the folded unit into the eye through an opening formed in the eye.

As will be seen, the lens unit is thereby typically folded to form an M-shape, as in cross section, in order to pass through a very small wound in the eye wall. In this regard, the lens unit may have haptics so as to be initially elongated, and the multiple folds are formed to extend in the lens elongation direction, i.e., to both haptics.

It is another object to provide a folding tool having a first set of at least three folding elements and a second set of at least two folding elements, and effecting relative movement of the sets to fold a lens unit extending between the sets. As will be seen, the folding elements of the tool are typically produced to extend in elongated, parallel directions, and may be narrow, i.e., to be wire-like.

Another object is to move the two sets of elements so the elements of the first set pass relatively between the elements of the second set, there being at least two elements in the second set, and at least three elements in the first set.

Yet another object is to provide the lens unit in folded state to have elongation between folded haptics at opposite ends of the unit, and the grasping pinches the folded unit to greater extent at a location medially of the unit than at locations proximate its ends.

An additional object is to provide for release of lens unit grasping after the lens unit has been inserted endwise into the eye, whereby completed unfolding of the unit folds at its opposite ends precedes completed unfolding of the folds at the medial location. In this regard, the lens unit grasping elements, such as arms, are provided to have lens unit pinching surfaces located to pinch the folded unit to greater extent at a location medially of the unit than at locations proximate its opposite ends. Such surfaces of the grasping tool typically have convex extents presented oppositely, toward opposite side folds of the folded unit.

Release of such a medially pinched lens thereby proceeds gradually, instead of explosively, with the medially pinched portion of the lens unit completing its unfolding after completion of unfolding of lens unit opposite ends, thereby minimizing potential impact damage to the eye structure.

A yet further object is to insert the multi-folded lens into the eye zone between the iris and cornea of the eye, via a very small eye wound opening, so that unfolding will not damage the natural lens or its surface. Subsequently, and after completion of lens unit unfolding, the reshaped lens unit is manipulated, a portion at a time, into the intraocular zone between the iris and the natural lens, for ultimate, safe placement adjacent the natural lens surface.

Additional objects include provision of apparatus or tools to accomplish multiple folding of a very small plastic lens unit, and its positioning in the eye, for safe unfolding, as referred to. As will appear, such apparatus typically includes elements to form at least three folds, and an M-shaped folded lens may be formed. As will be seen, there may be two sets of such elements supported for movement carrying the elements of one set between the elements of the other set, during folding of a lens located between the sets.

These and other objects and advantages of the invention, as well as the details of an illustrative embodiment, will be more fully understood from the following specification and drawings, in which:

DETAILED DESCRIPTION

Figures 1, 1A:
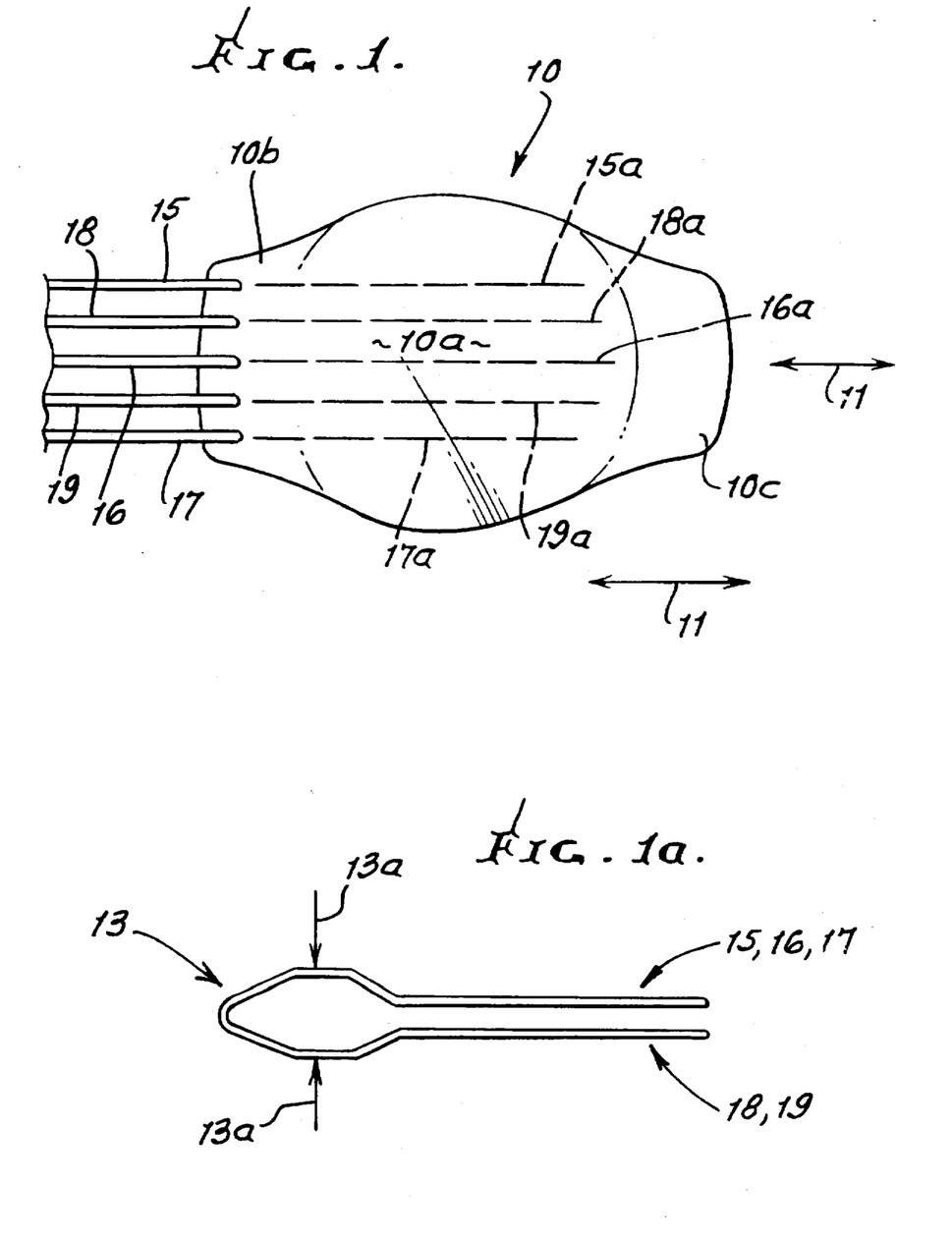
FIG. 1 is a plan view of an artificial lens and multiple elongated folding elements.
FIG. 1a shows a holder for such elements.
Figure 2:
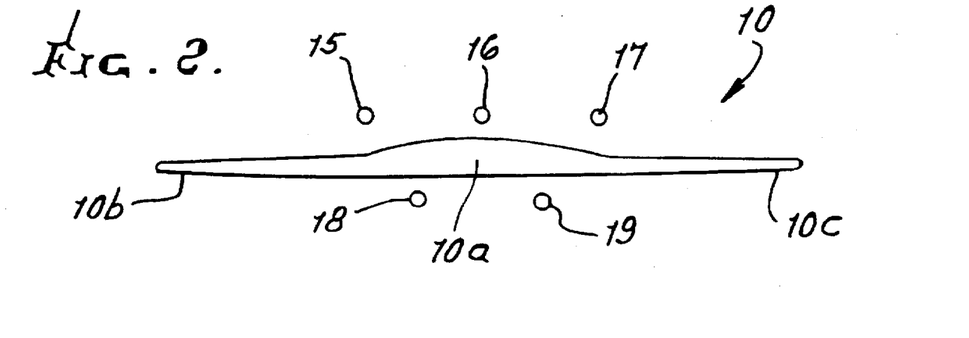
FIG. 2 is an elevation showing the lens positioned between multiple upper and lower folding elements.

In FIGS. 1 and 2, a plastic lens unit 10 has a central, generally circular, relatively thicker, zone 10a, and two tabular haptics 10b and 10c. The unit is elongated in direction 11, and its thickness decreases as shown at the haptics. The lens unit may typically be sized and constructed for insertion into the inter-ocular zone of the eye, between the cornea and natural lens, to be allowed to controllably unfold, as in the sub-zone between the iris and the cornea, i.e., spaced from the natural lens for maximum protection of the natural lens, during unfolding. Means is provided for folding the lens unit at multiple locations, to form at least three folds, such as accordion folds.

In FIG. 1, the parallel fold bend locations are seen at 15a–19a, in alignment with the fold forming parallel elements, such as wires or thin rods 15–19, respectively. These include two sets, i.e., one set of two elements 18 and 19, and another set of three elements 15, 16 and 17. In FIG. 2, the two sets are spaced apart, vertically, to allow placement of the lens unit 10 between them. FIG. 1a shows a holder 13 for the elements. Arrows 13a show manual face application to the holder to cause element movement as in FIGS. 3–5.

Figure 3:
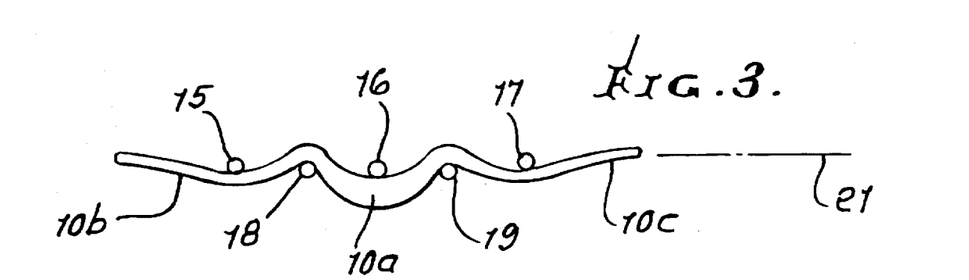
FIG. 3 is a view like FIG. 2 but showing the spacing between upper and lower folding elements reduced.

FIG. 3 shows the two sets moved toward one another to bring them into a common plane 21, with consequent initial folding of the lens unit, as shown.

Figure 4:
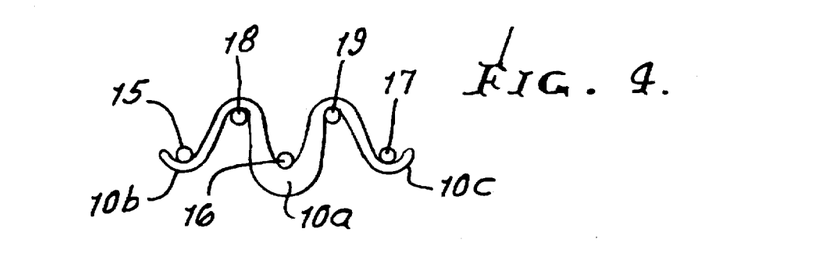
FIG. 4 is a view like FIG. 3 but showing the upper folding elements having been displaced to pass between the lower folding elements, to fold the lens at multiple fold locations.
Figure 5:
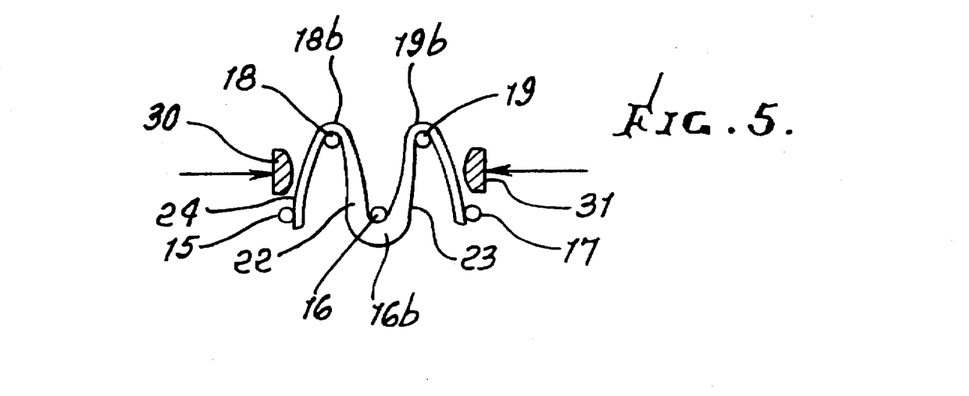
FIG. 5 is a view like FIG. 4 but showing the lens folded more extremely, with folds approaching one another, due to further relative displacement of the folding elements.

FIG. 4 shows the set of elements 18 and 19 as having passed relatively upwardly through and past the set of elements 15, 16, and 17, to increasingly fold the lens unit; and FIG. 5 shows even further upward relative displacement of the set 18 and 19. As a result, the lens unit is folded into M shape, with intermediate folds 22 and 23, and outer side folds 24 and 25. Bends appear at 18b and 19b, and at 16b. Bend 16b is at the thickest zone 10a part of the lens, whereas bends 18b and 19b are at thinner parts of the lens unit.

Figure 6:
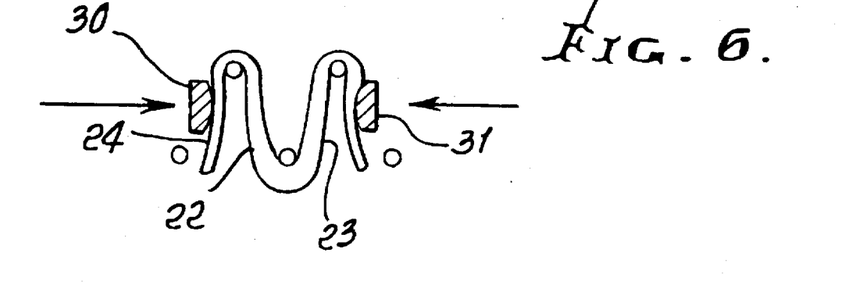
FIG. 6 is a view like FIG. 5 but showing grasping elements approaching the outermost folds.
Figure 7:
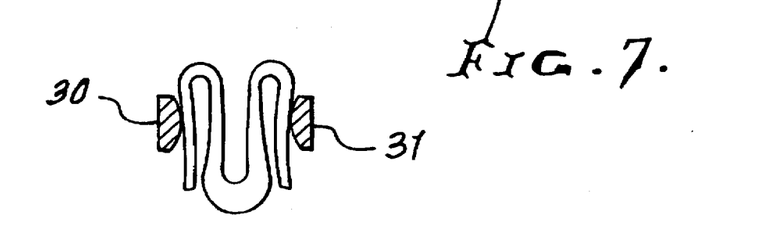
FIG. 7 is a view like FIG. 6 but showing the lens folds pushed more closely together by the lens grasping elements.
Figure 8:
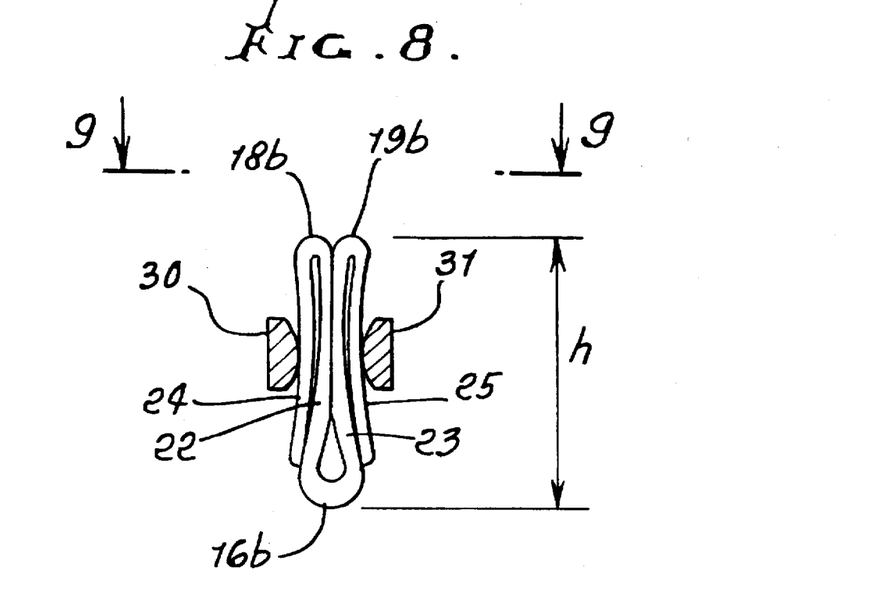
FIG. 8 is a view like FIG. 7 but showing the lens folds variably pinched together by the grasping elements, in preparation for insertion through a very small eye wound opening into the eye.
Figure 9:
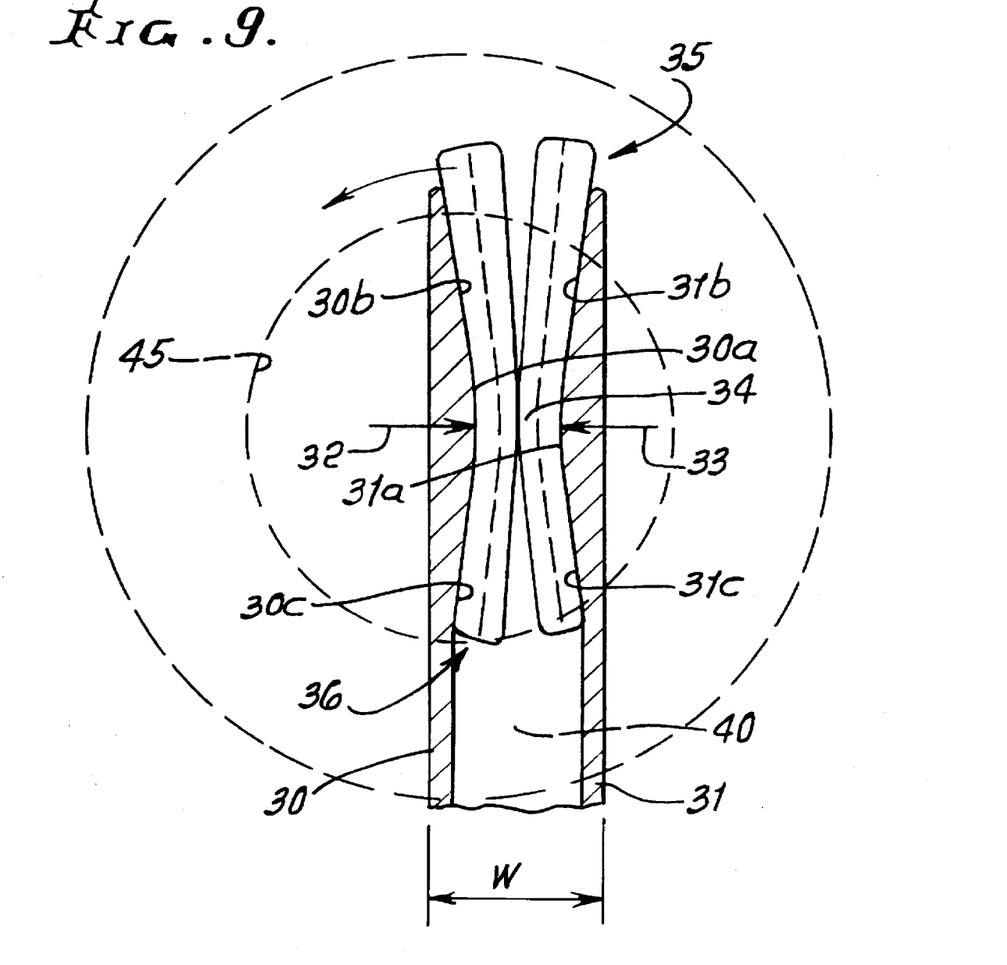
FIG. 9 is an enlarged view taken on lines 9—9 of FIG. 8 showing the multi-folded lens inserted into the eye between the iris and the cornea.

As the lens unit folding nears completion, the unit is grasped to hold it in folded state, for insertion into the eye, as represented in FIG. 9. In this regard, parallel, rod-like grasping units 30 and 31 are displaced toward one another, as represented in FIGS. 5, 6, and 7, to grasp the outer side folds 24 and 25, to urge them toward one another, collapsing the lens unit into final folded state, as seen in FIG. 8, with side folds 24 and 25 pressed toward intermediate folds 22 and 23 forming a stacked relationship at the fold lengthwise intermediate extents. See arrows 32 and 33 representing force exerted by convex intermediate sides 30a and 31a of the elongated grasping units or tongs 30 and 31 in FIG. 9. A compressed pinch effect is thereby produced at region 34, intermediate or medial, for reasons as will appear.

Opposite end portions of the folded lens unit, as at regions generally designated at 35 and 36, are not pinched together, but may flare apart slightly as shown. Note that the facing sides of the tongs, as at 30b and 31b are spaced apart to greater extent than at 30a and 31a, this relationship also appearing at 30c and 31c, to produce such flaring.

FIGS. 8 and 9 show the folded lens unit occupying minimum width "w", and minimum height "h", for entry through a minimum height and width wound at 40 in the wall of the eye.

That wound may, for example, have a slit length of about 0.5 to 2 mm or larger. The smallness of the wound results in minimum disruption of the eye, and promotes faster healing. The insertion techniques, as disclosed herein, also promote faster surgery.

Note in FIG. 9 that the folded unit may be inserted in offset relation to the center of the eye, as defined by the iris opening 45. The insertion tool handles or arms 46 and 47, attached to the lens-grasping units 30 and 31, may be maneuvered to position the folded lens in centered relation to the iris.

Figure 10:
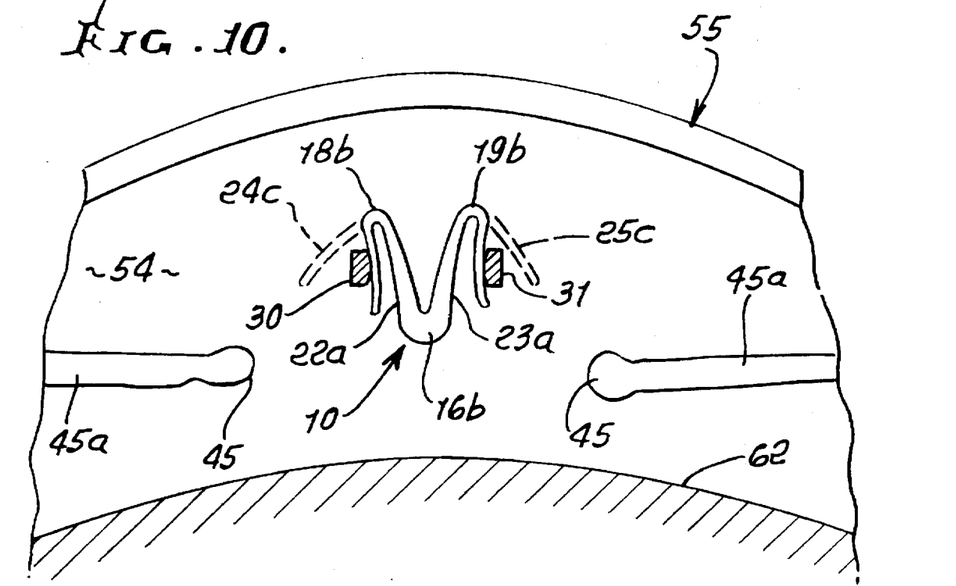
FIGS. 10–12 are elevations showing progressive release of the folded lens in the eye, in response to separation of the grasping elements.

FIG. 10 shows the positioning of the folded lens unit in the chamber 54 between the iris 45a and the cornea 55. As the grasping elements 30 and 31 are moved apart, the opposite end portions of the lens outer folds, as represented at 24c and 25c, spread apart to greater extent than the mid portions of the inner folds seen at 22a and 23a, whereby an explosive unfolding of the lens is prevented.

Figure 11:
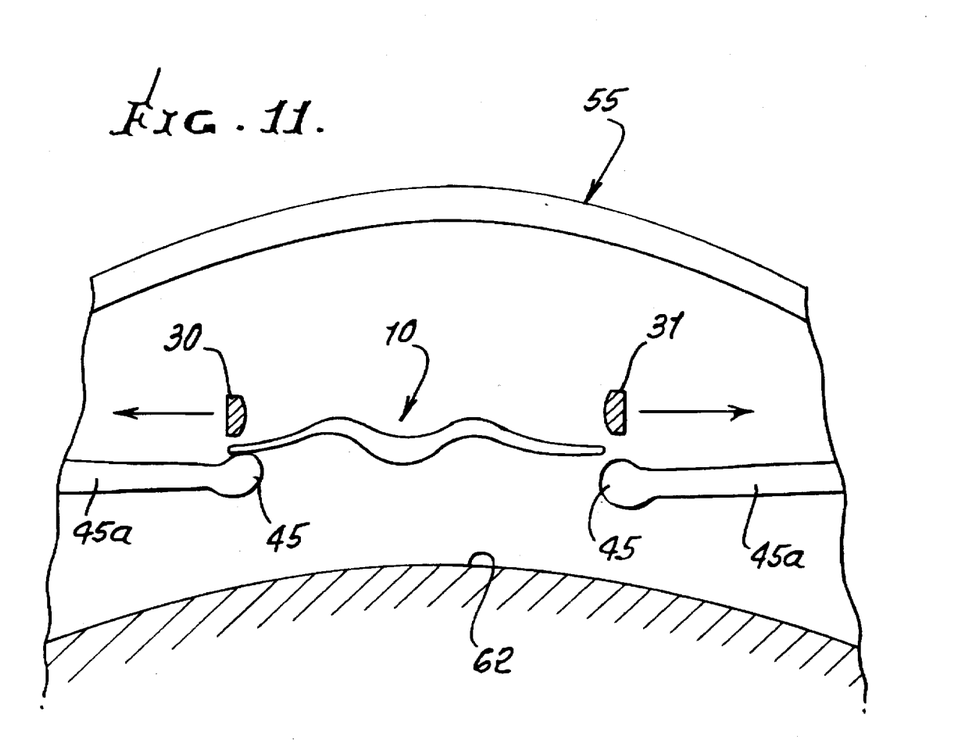

Thus, as seen in FIG. 11, by the time that the thicker folds 22 and 23 are allowed to spread apart, as by retraction of 30 and 31, the outer folds have almost completely unfolded toward the iris portion 45b.

Figure 12:
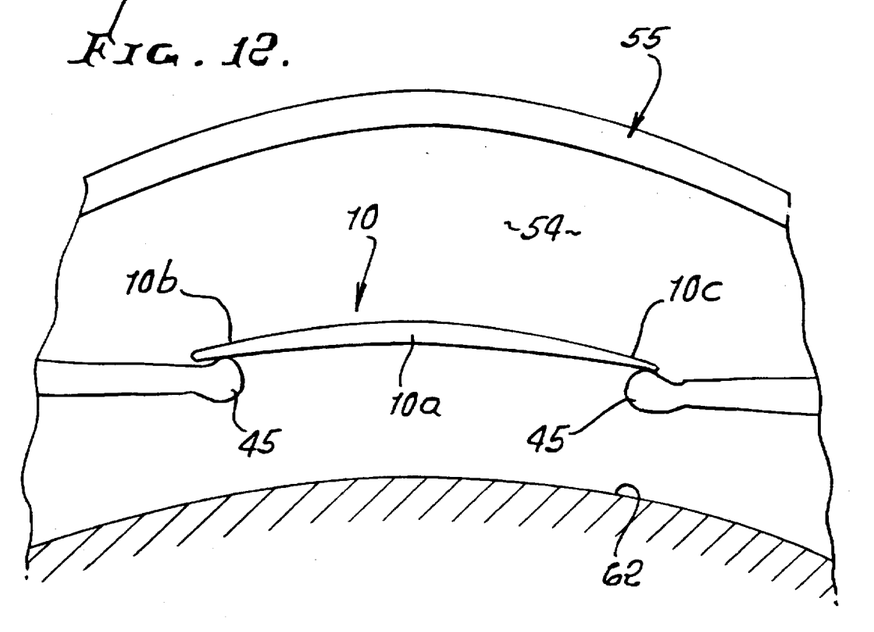

FIG. 12 shows the completely unfolded lens unit, positioned just above the iris.

Figure 13:
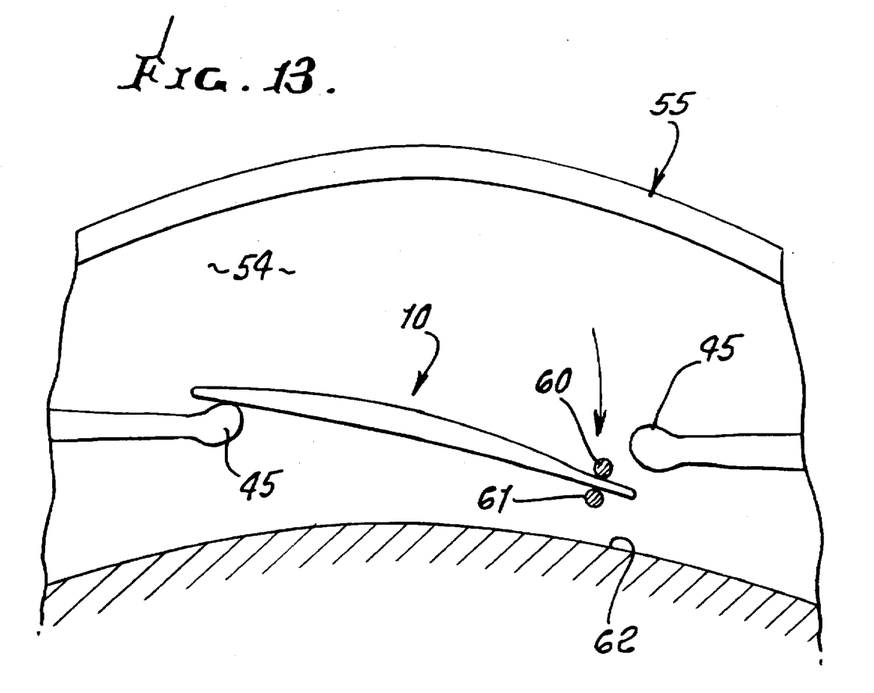
FIG. 13 is a view showing haptic or lens edge portion, being displaced below the iris and toward the natural lens of the eye.
Figure 14:
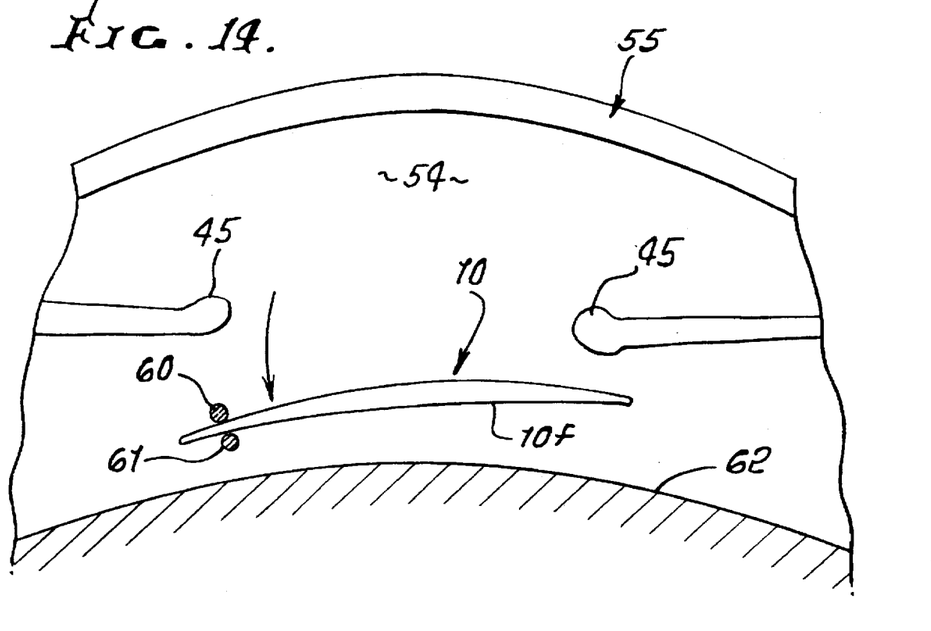
FIG. 14 is a view like FIG. 13 showing another haptic, or lens edge portion, being displaced below the iris and toward the natural lens of the eye, the entire lens then positioned below the iris.

FIG. 13 shows use of a tool having arms 60 and 61 maneuvering one end of the lens unit into the space below the iris and toward natural lens surface 62; and FIG. 14 shows use of that tool to maneuver the opposite end of the lens unit below the iris, in position for application to the natural lens surface.

Figure 15:
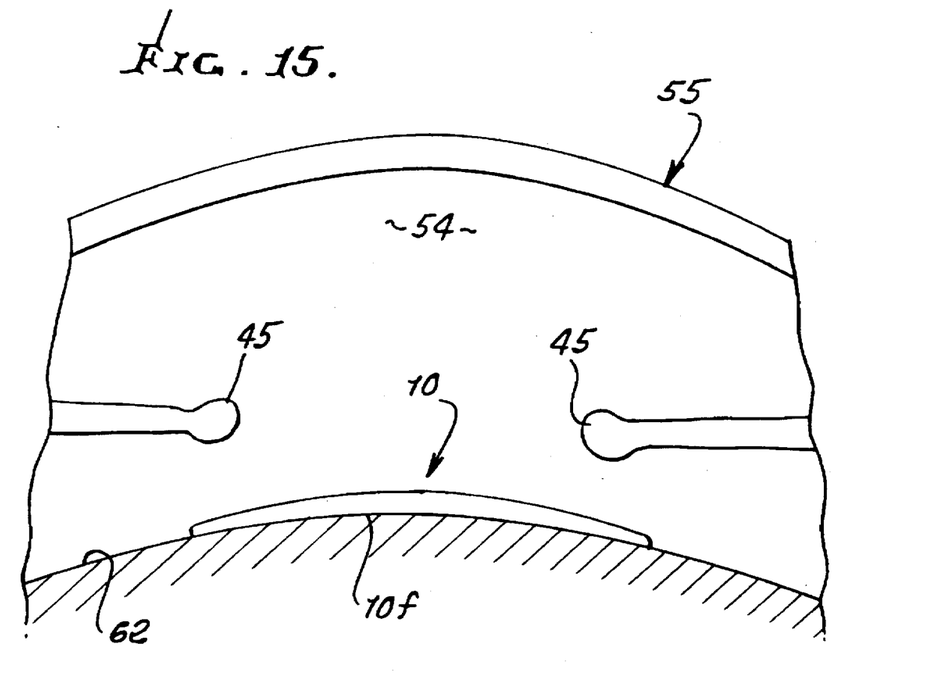
FIG. 15 is a view like FIG. 14 showing the artificial lens positioned directly adjacent the surface of the natural lens.

FIG. 15 shows the unfolded lens with its lower concave side 10f very closely positioned proximate the natural lens surface 62, as described.

Figure 16:
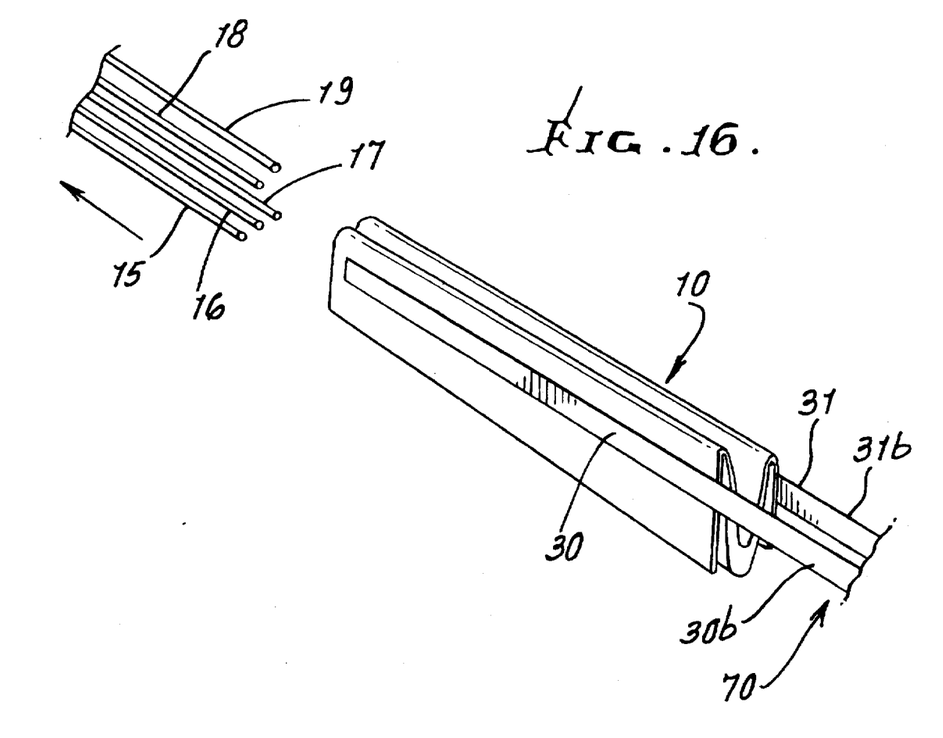
FIG. 16 is a perspective view of lens folding elements, and a lens grasping tool, as they are related during use.

FIG. 16 is a perspective view showing the folded lens unit 10, held as in FIG. 8 by the blades or lens grasping arms 30 and 31 of the tool 70, as the lens-folding elements 15–19 are retracted endwise to free them from the folded lens unit. Arm extensions 30b and 31b are suitably manipulable to move the elements 30 and 31 toward and away from one another.

The lens insert 10 is characteristically very thin and highly light refractive.

Figure 17:
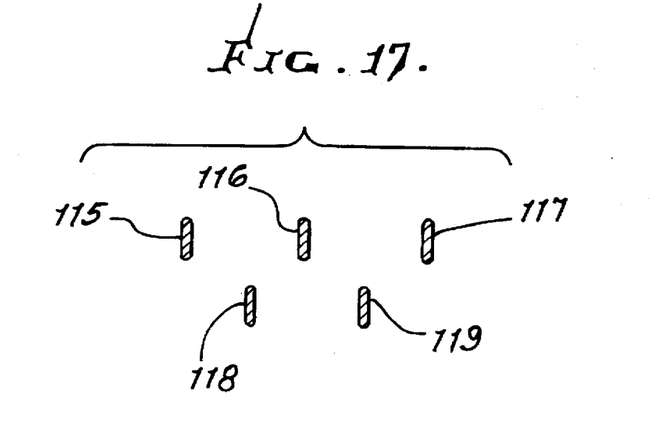
FIG. 17 is an end view of modified folding elements.

FIG. 17 is an end view of modified folding elements 115–119 corresponding to elements 15–19. Elements are vertically elongated, in cross section, to resist bending, as the lens unit is folded therebetween. FIGS. 1–16 may be regarded as showing preferred aspects of the invention.

I claim:

1. In the method of inserting a foldable plastic lens unit into the eye, the steps that include a) folding the lens unit to form at least three folds, b) providing a grasping tool grasping and pinching the folded unit by use of said tool to hold the unit in folded state, with the folds compressed in side-by-side generally parallel condition, and then inserting the folded unit into the eye through an opening formed in the eye.

2. The method of claim 1 wherein the lens unit is folded to form an M shape.

3. The method of claim 1 wherein the lens unit has haptics and is initially elongated, and said folds are formed to extend with elongation to both haptics.

4. The method of claim 1 wherein the lens unit in completely folded state and in M configuration has elongation between folded haptics at opposite ends of the unit, and said grasping pinches the completely folded unit to greater extent at a location or locations medially of the unit than at locations proximate said ends.

5. The method of claim 1 wherein said inserting positions the folded unit in the eye zone between the iris and the cornea of the eye.

6. The method of claim 5 including releasing the grasping of the folded unit to allow the unit to unfold in said eye zone, the lens unit having a lens which is thereby presented toward the natural lens of the eye.

7. The method of claim 6 including manipulating said unfolded unit to extend in the intraocular eye zone between the iris and the natural lens of the eye.

8. The method of claim 7 wherein said manipulating includes i) first deflecting a first edge portion of the unit into said eye zone between the iris and the natural lens, and ii) subsequently deflecting a second edge portion of the unit into said eye zone between the iris and the natural lens.

9. In the method of inserting a foldable plastic lens unit into the eye, the steps that include a) providing a folding tool having a first set of three folding elements and a second set of two folding elements, and effecting relative movement of said sets to fold a lens unit extending between said sets, thereby to form at least three folds, b) and thereafter grasping the folded unit to hold it in folded state, and then inserting the folded unit into the eye through an opening formed in the eye.

10. The method of claim 9 wherein said elements are provided to extend in elongated, parallel relation.

11. The method of claim 10 including endwise relatively withdrawing said folding elements from the folded lens unit after said grasping of the unit has been at least initially effected.

12. The method of claim 9 wherein the folding elements of the second set are relatively moved between the folding elements of the first set during said lens folding, there being at least two elements in the second sets, and three elements in the first set.

13. The method of claim 12 including releasing said grasping after the lens unit has been inserted endwise into the eye, whereby completed unfolding of the unit at its said opposite ends precedes completed unfolding of the folds at said medial location.

14. The method of claim 12 wherein said grasping of the folded unit includes providing additional elongated grasping elements, and moving said elements into grasping relation with the folds of said unit that are presented outermost.

15. The method of claim 14 wherein said grasping elements are provided to have lens unit pinching surfaces located to pinch the folded unit to greater extent at a location medially of the unit than at locations proximate said ends.

16. The method of claim 15 wherein said pinching surfaces are provided to have convex extents presented oppositely, toward opposite sides of the folded unit.

* * * * *